(12) United States Patent
    Neumann

(10) Patent No.: US 12,073,294 B2
(45) Date of Patent: Aug. 27, 2024

(54) METHOD OF AND SYSTEM FOR GENERATING A STRESS BALANCE INSTRUCTION SET FOR A USER

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 1049 days.

(21) Appl. No.: 16/939,244

(22) Filed: Jul. 27, 2020

(65) Prior Publication Data

US 2022/0027783 A1    Jan. 27, 2022

(51) Int. Cl.
| | |
|---|---|
| *G06N 20/00* | (2019.01) |
| *G06F 16/242* | (2019.01) |
| *G16H 10/60* | (2018.01) |
| *G16H 20/70* | (2018.01) |
| *G16H 50/20* | (2018.01) |
| *G16H 50/30* | (2018.01) |

(Continued)

(52) U.S. Cl.
CPC ......... *G06N 20/00* (2019.01); *G06F 16/2433* (2019.01); *G16H 10/60* (2018.01); *G16H 20/70* (2018.01); *G16H 50/20* (2018.01); *G16H 50/30* (2018.01); *G16H 50/50* (2018.01); *G16H 50/70* (2018.01)

(58) Field of Classification Search
None
See application file for complete search history.

(56) References Cited

U.S. PATENT DOCUMENTS

| | | | |
|---|---|---|---|
| 9,955,902 B2 | 5/2018 | Frank et al. | |
| 2012/0179481 A1* | 7/2012 | Patel | G06Q 30/02 705/2 |
| 2016/0300252 A1 | 10/2016 | Frank et al. | |

(Continued)

OTHER PUBLICATIONS

Amazon Web Services, Amazon SageMaker Ground Truth, 2019, https://aws.amazon.com/sagemaker/groundtruth/ (Year: 2019).*

(Continued)

*Primary Examiner* — Devin C Hein
(74) *Attorney, Agent, or Firm* — Caldwell Intellectual Property Law

(57) ABSTRACT

A system for generating a stress balance instruction set for a user, the system comprising a computing device, wherein the computing device is configured to receive a plurality of user data to calculate a stress score of a user. Calculating the stress score further comprises training a machine-learning model as a function of stress score training data that numerically describes stress in a user. Computing device generates a plurality of user metrics as a function of the plurality of user data and the machine-learning model and calculates an overall stress score. Computing device determines a stress imbalance using the overall stress score by training a machine-learning model and determining any difference between an anticipated normal stress score and user the stress score. Computing device generates a stress balance instruction set by training a machine-learning model, identifying a strategy, and generating an instruction set for implementing the strategy.

18 Claims, 8 Drawing Sheets

(51) Int. Cl.
*G16H 50/50* (2018.01)
*G16H 50/70* (2018.01)

(56) References Cited

U.S. PATENT DOCUMENTS

| | | | | |
|---|---|---|---|---|
| 2016/0306844 | A1 | 10/2016 | Frank et al. | |
| 2017/0213007 | A1* | 7/2017 | Moturu | G16H 20/10 |
| 2018/0107943 | A1* | 4/2018 | White | G06N 5/01 |
| 2019/0189025 | A1* | 6/2019 | Angelopoulos | G16H 20/10 |
| 2019/0385711 | A1* | 12/2019 | Shriberg | G16H 50/20 |
| 2020/0411185 | A1* | 12/2020 | Oser | G16H 50/20 |
| 2021/0225507 | A1* | 7/2021 | Van Kollenburg | G16H 50/70 |
| 2021/0335478 | A1* | 10/2021 | Kulkarni | G16H 10/60 |
| 2021/0335491 | A1* | 10/2021 | Morris | G16H 50/50 |

OTHER PUBLICATIONS

Barbosa CD, Balp MM, Kulich K, Germain N, Rofail D. A literature review to explore the link between treatment satisfaction and adherence, compliance, and persistence. Patient Prefer Adherence. 2012;6:39-48. doi: 10.2147/PPA.S24752. Epub Jan. 13, 2012. PMID: 22272068; PMCID: PMC3262489. (Year: 2012).*

* cited by examiner

METHOD OF AND SYSTEM FOR GENERATING A STRESS BALANCE INSTRUCTION SET FOR A USER

FIELD OF THE INVENTION

The present invention generally relates to the field of machine-learning. In particular, the present invention is directed to a system for generating a stress balance instruction set for a user.

BACKGROUND

To assist individuals in managing their day-to-day lives and better control their stress levels, coaches and psychologists often attempt to analyze life events to determine stressors that may lead to stress imbalance and/or causes that may contribute to stress imbalance. Being aware of these stressors can be the first step in assisting individuals with navigating challenging events and may help enable them to improve their lifestyle through better choices to manage their stress. However, stressor analysis is typically performed after a traumatic event and mathematically evaluating stress remains difficult for practitioners. This leaves individuals with few options for personalized stress analysis including techniques for measuring stress, adopting stress management strategies, and potentially reducing the impact of future stressors.

SUMMARY OF THE DISCLOSURE

In an aspect, a system for generating a stress balance instruction set for a user, the system comprising a computing device, wherein the computing device is configured to receive a plurality of user data to calculate a user stress score. Computing device may calculate the stress score using a machine-learning model trained as a function of stress score training data that delineates stress in a user. Computing device may then generate a plurality of user metrics as a function of the plurality of user data wherein a machine-learning model may calculate an overall stress score. Computing device may determine a stress imbalance comparing the overall stress score to a normal stress threshold by training a machine-learning model with data corresponding to metrics in normal stress baselines, and determine any differences between an anticipated normal stress score and the user stress score. Computing device may generate a stress balance instruction set to address a stress imbalance by using a machine-learning process, identifying a strategy, generating an instruction set for implementing the strategy, and determining the effectiveness of a strategy for a user.

In another aspect, a method for generating a stress balance instruction set for a user, the system comprising a computing device, wherein the computing device is configured to receive a plurality of user data to calculate a user stress score. Computing device may calculate the stress score using a machine-learning model trained as a function of stress score training data that delineates stress in a user. Computing device may then generate a plurality of user metrics as a function of the plurality of user data wherein a machine-learning model may calculate an overall stress score. Computing device may determine a stress imbalance comparing the overall stress score to a normal stress threshold by training a machine-learning model with data corresponding to metrics in normal stress baselines, and determine any differences between an anticipated normal stress score and the user stress score. Computing device may generate a stress balance instruction set to address a stress imbalance by using a machine-learning process, identifying a strategy, generating an instruction set for implementing the strategy, and determining the effectiveness of a strategy for a user.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a stress balance instruction set for a user. In an embodiment, a computing device may train a machine-learning model in evaluating stressors in user input data by determining stress metrics that relate an overall stress score of a user to events in their life and the impact they have on user stress. Computing device may use a machine-learning model to train using datasets that correspond to normal stress thresholds for comparing a user stress score to determine stress imbalances. Computing device may user a machine-learning model to train using datasets that correspond strategies to stress imbalances. A machine-learning process may provide an instruction set to implementing a suitable stress management strategy and iteratively improve the impact of recommendations in instruction sets by receiving updated user data and determining the effectiveness of strategies as adopted by a user.

Figure 1:
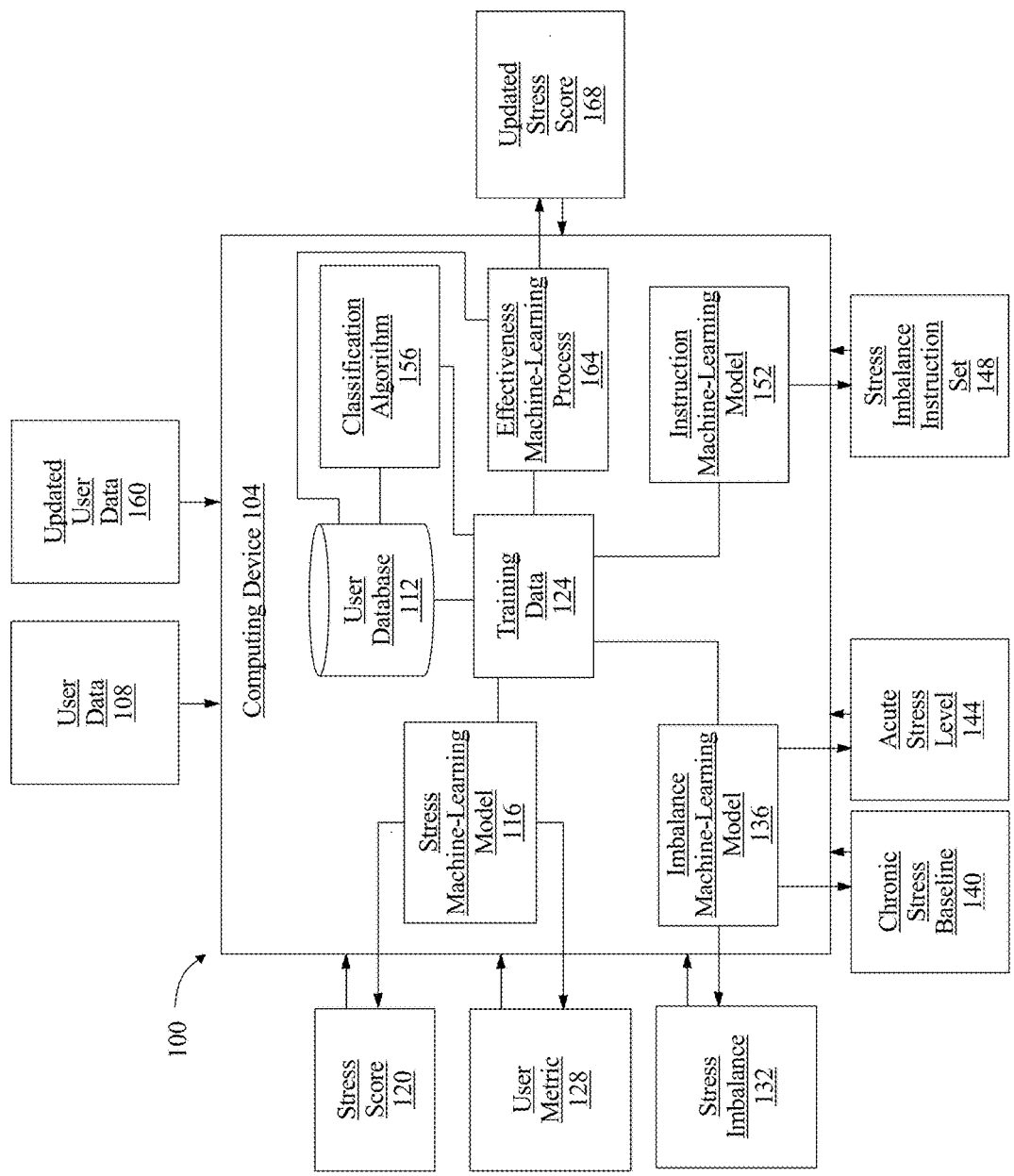
FIG. 1 is a block diagram of an exemplary embodiment of a system for generating a stress balance instruction set for a user.

Referring now to FIG. 1, an exemplary embodiment of a system 100 for generating a stress balance instruction set for a user is illustrated. System 100 includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially and the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, and the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing in reference to FIG. 1, computing device 104 may be configured to receive a plurality of user data 108. User data 108 may refer to measurement a physiological signal, for instance blood pressure, sleep quality, lifestyle data, demographics, age, and the like, of the user, behavioral cue of the user, for instance anger management ability, social anxiety, and the like, and/or any data relating to an affective response of a user. User data 108 may refer to a measurement of affective response and may include one or more raw values and/or processed values, for instance, resulting from filtration, calibration, and/or feature extraction of a device, such as a wearable device, sensor, and the like, that is meant to measure, record, and/or analyze user data 108. A wearable device may be coupled to the body of a user in various ways. For instance in non-limiting examples, a sensor may be a device that is implanted in the user's body, attached to the user's body, embedded in an item carried and/or worn by the user, for instance, a sensor may be embedded in an electronic device, clothing, and/or remote from the user, for instance a camera feed, and the like.

Herein, "affect" and "affective response" may refer to physiological and/or behavioral manifestation of an entity's stress level. The manifestation of an entity's stress level may be referred to herein as an "emotional response" and may be used interchangeably with the term "affective response". Affective response typically refers to values obtained from measurements and/or observations of an entity, while stress levels are qualitatively and/or quantitatively determined from models and/or reported by the entity feeling an effect of stress from a stressor. In non-limiting illustrative examples, a user's stress level may be determined based on measurements of the person's affective response, for instance from a combination of wearable device data and user input. In addition, the terms "level" and "imbalance", when used in phrases such as "stress level" or "stress imbalance", may be used herein interchangeably. However, in the way the terms are typically used, the term "level" may refer to designate a condition which a user is in, has arrived at, or may arrive at, and the term "imbalance" may refer to an offset of the user due to the condition the user is in, and/or due to a change in the condition the user is in from a predicted, calculated, or otherwise determined "normal threshold" from which the imbalance is determined.

It is to be noted that as used in this disclosure, a "user data" may comprise one or more qualitative and/or quantitative values describing a physiological signal, behavioral cue, and/or affective response of a user, which may be obtained directly from a user, provided by a user, and/or supplied by an individual who is not the user such as a medical professional, mental health care professional, caretaker, of the like. Alternatively or additionally, user data 108 data may include a "raw" measurement of an affective response, wherein a computing device 104 may calculate, measure, extrapolate, or otherwise determine using, for instance and without limitation, a machine-learning model a metric, such as a stress level. For instance in non-limiting examples, a measurement of an affective response contained in user data 108 may be represented by any type of numerical value returned by a sensor, such as a heart rate, neural activity pattern, recording of facial expression, and the like, that is organized in a table, matrix, vector, among other forms, that a computing device 104 may receive as user data 108 to determine a user metric as it relates to a stress score, as described in further detail below.

An "event" and/or "user experience," as used herein, may involve an event and/or experience that occurs within proximity to a user, with a user's participation, and/or that has an effect—noticeable by the user or not—on a user, which may affect the overall stress level of the user in some manner that may be detected by measuring the affective response of the user as reflect in the user data 108. In non-limiting illustrative examples, user events and/or experiences may belong to different groups and/or types, such as being at a location, consuming certain content, having a social interaction, such as in physical presence or via a virtual environment, exercising, traveling a certain route, consuming a substance, and/or utilizing a product. In some embodiments, experiences may involve activity in the physical world, for instance spending time at a hotel or being at work, and/or experiences may involve activity in virtual environments, such as online shopping, social media use, or spending time in a videoconference. In some embodiments, an experience is something a user actively chooses to participate in and is aware of; for example, the user may choose to take a vacation. While in other embodiments, an experience may be something that happens to the user, of which the user may not be aware. For example, a user may be overtraining in their exercise routine; this example may correspond to an experience of exercising in which the user is aware, but the user may not be aware that the level of exercise is in the 'overtraining range' for the user. A user may have the same experience multiple times during different periods, wherein the period in which the experience occurs is important to the context of the experience. For example, the experience of being at school may happen to certain users every weekday, except for holidays and/or weekends. Each time a user has an experience, this may be considered an "event". Each event has a corresponding experience and a corresponding user (who had the corresponding experience). Additionally, an event may be referred to as being an "instantiation" of an experience and the time during which an instantiation of an event takes place, may be referred to herein as the "instantiation period" of the event. That is, the instantiation period of an event is the period of time during which the user corresponding to the event had the experience corresponding to the event. Optionally, an event may have a corresponding measurement of affective response, which is a measurement of the corresponding user to having the corresponding experience (during the instantiation of the event or shortly after it). User data 108 and all related elements may be stored and/or retrieved from a user database 112, as described in further detail below.

Figure 2:
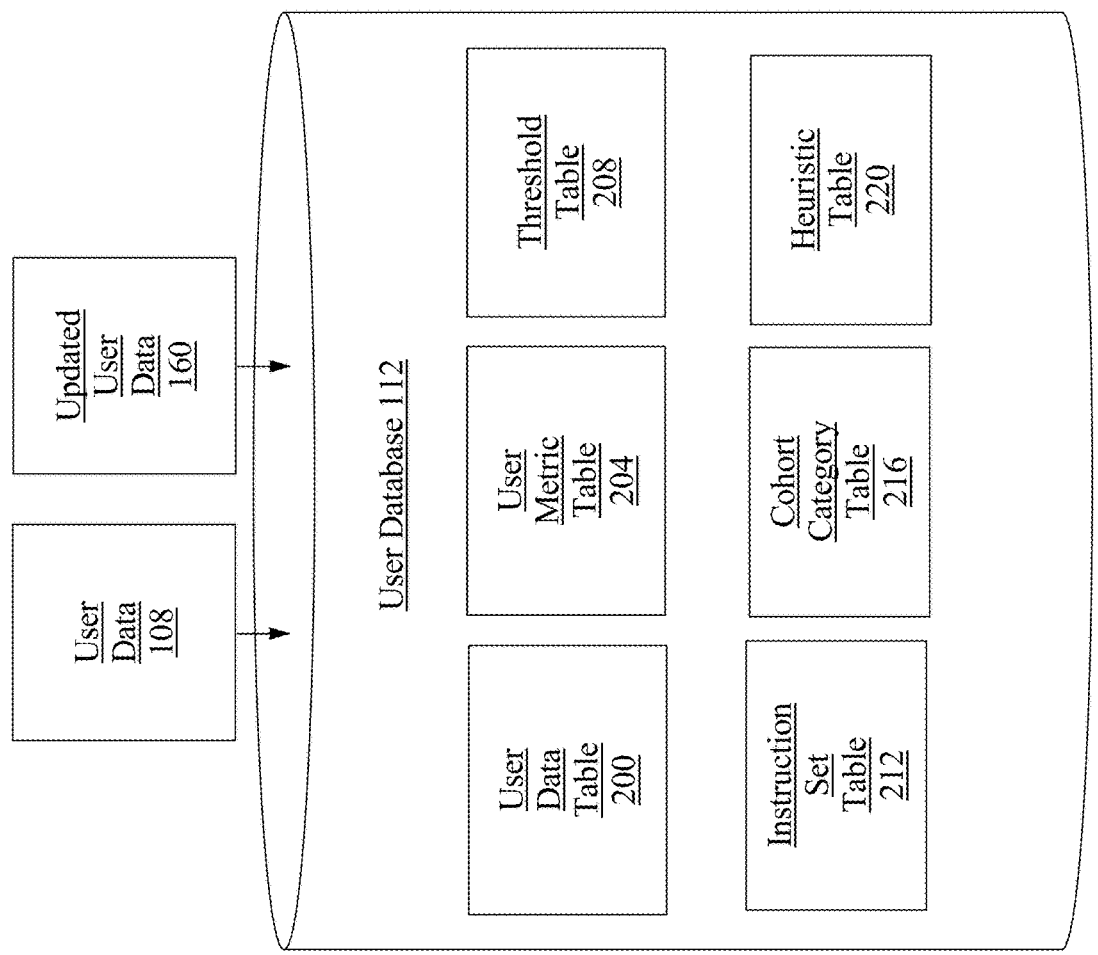
FIG. 2 is a block diagram illustrating an exemplary embodiment of a user database.

Referring now to FIG. 2, a non-limiting exemplary embodiment of a user database 112 is illustrated. User database 112 may be implemented, without limitation, as a relational database, a key-value retrieval database such as a NOSQL database, or any other format or structure for use as a database that a person skilled in the art would recognize as suitable upon review of the entirety of this disclosure. User database 112 may alternatively or additionally be implemented using a distributed data storage protocol and/or data structure, such as a distributed hash table and the like. User database 112 may include a plurality of data entries and/or records as described above. Data entries in a user database 112 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Further referring to FIG. 2, user database 112 may include, without limitation, a user data table 200, user metric table 204, threshold table 208, instruction set table 212, cohort category table 216, and/or heuristic table 220. Determinations by a machine-learning process, machine-learning model, and/or scoring function may also be stored and/or retrieved from the user database 112, for instance in non-limiting examples a classifier describing a subset of stress management strategies as it relates to a stress imbalance and/or stress score, as described in further detail below. Determinations by a machine-learning model for calculating a stress score and/or a stress threshold may also be stored and/or retrieved from the user database 112, as described in further detail below. As a non-limiting example, user database 112 may organize data according to one or more instruction tables. One or more user database 112 tables may be linked to one another by, for instance in a non-limiting example, common column values. For instance, a common column between two tables of user database 112 may include an identifier of a submission, such as a form entry, textual submission, research paper, and the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, and the like; persons skilled in the art, upon reviewing the entirety of this disclosure, will be aware of various ways in which data from one or more tables may be linked and/or related to data in one or more other tables.

Still referring to FIG. 2, in a non-limiting embodiment, one or more tables of a user database 112 may include, as a non-limiting example, a user data table 200, which may include wearable device data, user-reported data, affective response measurements, and the like, for use in determining user metrics, stress scores, training machine-learning models, and the like, correlating user data to other tables, entries indicating degrees of relevance to and/or efficacy in calculating a metric, quantifier, score and/or stress level, user metrics as it relates to stress, and/or other elements of data computing device 104 and/or system 100 may store, retrieve, and use to determine usefulness and/or relevance of user data in determining stress level, user events, scores, thresholds and/or instruction sets for stress management as described in this disclosure. One or more tables may include user metric table 204, which may include a history of numerical values, metrics, functions, vectors, matrices, and the like, for instance and without limitation, that quantify or otherwise summarize user physiology, affective response, and the like, for instance a history and tabulation of sleep quality scores determined from a combination of EEG, ECG, bioimpedance, and user-reported data. One or more tables may include a threshold table 208, which may correlate user metrics, stress score, and/or user data 108 as it pertains to a first user and/or other users, including any outcomes, models, heuristics, scores and/or combinations thereof as they may correspond to other users and/or overall numerical values, ranges of values, metrics, functions, vectors, matrices, and the like, that corresponds to an overall measure, or range, of user stress level and associated wellness that can be used to determine if a user experiences a stress imbalance, has performed an instruction set, and the like. One or more tables may include, without limitation, an instruction table 212 which may contain one or more inputs identifying one or more categories of data, for instance a set of instructions describing steps to implementing a stress management strategy, the number and type of user activities for improving a stress score, anticipated, measured, or otherwise calculated effects of instructions on a stress score, and the like. One or more tables may include, without limitation, a cohort category table 216 which may contain one or more inputs identifying one or more categories of data, for instance subsets of user metrics, stress scores, thresholds, instructions, effectiveness of instructions, and the associated effects instructions may have had on the metrics, scores, and/or thresholds from one or more users with regard to training and/or generation of objective functions, machine-learning models, scoring functions, ranking functions, and/or user instruction sets as a result of, for instance and without limitation, outputting elements and/or other user data input elements. One or more tables may include, without limitation, a heuristic table 220, which may include one or more inputs describing potential mathematical relationships between at least an element of user data and, for instance and without limitation, stress scores, instructions, and rankings thereof, change in user score over time as a function of effectiveness of an instruction set, and/or ranking functions for priority of instructions, as described in further detail below.

Referring back to FIG. 1, computing device 104 may calculate using a stress machine-learning model 116 and a plurality of user data 108, a stress score 120 of a user, wherein calculating a stress score 120 may include training a stress machine-learning model 116 as a function of stress score 120 training data 124, wherein training data 124 includes a plurality of entries, and each entry correlates user data to at least a user metric that delineates stress in a user, as described in further detail below.

Continuing in reference to FIG. 1, "training data," as used herein, is data containing correlations that a machine-learning process may use to model relationships between two or more categories of data elements. For instance, and without limitation, training data 120 may include a plurality of data entries, each entry representing a set of data elements that were recorded, received, and/or generated together; data elements may be correlated by shared existence in a given data entry, by proximity in a given data entry, and the like. Multiple data entries in training data 120 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 120 according to various correlations; correlations may indicate causative and/or predictive links between categories of data elements, which may be modeled as relationships such as mathematical relationships by machine learning processes as described in further detail below. Training data 120 may be formatted and/or organized by categories of data elements, for instance by associating data elements with one or more descriptors corresponding to categories of data elements. As a non-limiting example, training data 120 may include data entered in standardized forms by persons or processes, such that entry of a given data element in a given field in a form may be mapped to one or more descriptors of categories. Elements in training data 120 may be linked to descriptors of categories by tags, tokens, or other data elements; for instance, and without limitation, training data 120 may be provided in fixed-length formats, formats linking positions of data to categories such as comma-separated value (CSV) formats and/or self-describing formats such as extensible markup language (XML), enabling processes or devices to detect categories of data.

Alternatively or additionally, training data 120 may include one or more elements that are not categorized; that is, training data 120 may not be formatted or contain descriptors for some elements of data. Machine learning algorithms and/or other processes may sort training data 120 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 120 to be made applicable for two or more distinct machine learning algorithms as described in further detail below. Training data 120 used by computing device 104 may correlate any input data as described in this disclosure to any output data as described in this disclosure. Training data may contain entries, each of which correlates a machine learning process input to a machine learning process output, for instance without limitation, one or more elements of meal ingredients to a task chain. Training data may be obtained from previous iterations of machine-learning processes, user database 112, user inputs, and/or expert inputs. Training a machine-learning model using training data may be performed using a machine learning module, as described in further detail below.

Figure 3:
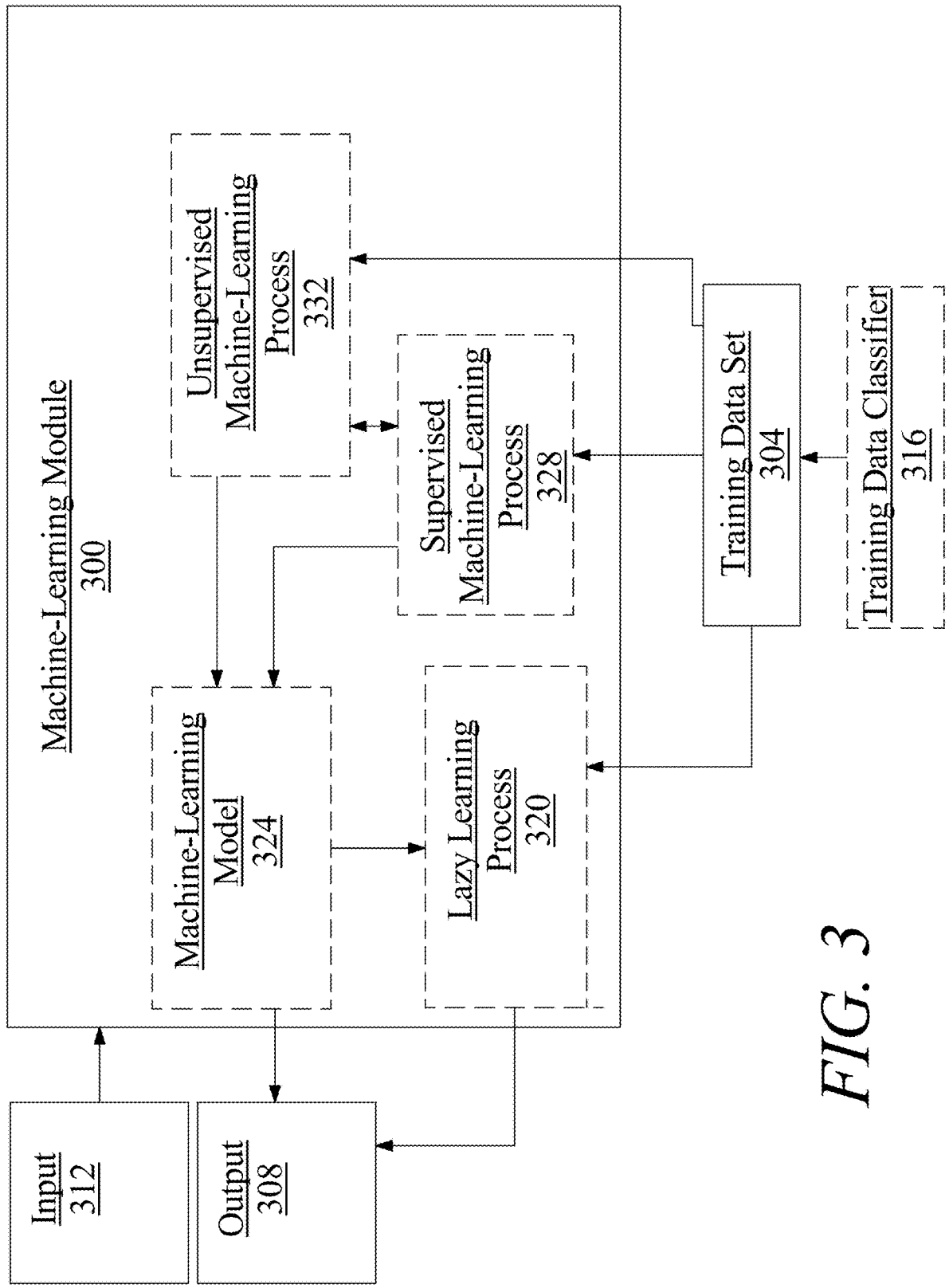
FIG. 3 is a block diagram illustrating an exemplary embodiment of a machine-learning module.

Referring now to FIG. 3, an exemplary embodiment of a machine-learning module 300 that may perform one or more machine-learning processes as described in this disclosure is illustrated. Machine-learning module may include any suitable machine-learning module which may perform determinations, classification, and/or analysis steps, methods, processes, and the like as described in this disclosure using machine learning processes. A "machine learning process," as used in this disclosure, is a process that automatedly uses training data set 304 containing training data 120 to generate an algorithm that will be performed by a computing device/module to produce outputs 308 given data provided as inputs 312; this is in contrast to a non-machine learning software program where the commands to be executed are determined in advance by a user and written in a programming language.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, and the like. Machine-learning module 300 may generate a classifier using a classification algorithm, defined as a process whereby a computing device and/or any module and/or component operating thereon derives a classifier from training data set 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to match one or more categories including elements of user data and/or constitutional data, such as without limitation a cohort of persons and/or other analyzed items and/or phenomena for which a subset of training data may be selected.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data set 304. Heuristic may include selecting some number of highest-ranking associations and/or training data set 304 elements. Lazy learning may implement any suitable lazy learning algorithm, including without limitation a K-nearest neighbors algorithm, a lazy naïve Bayes algorithm, and the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data set 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include identifications of meals 108 as described above as inputs, plurality of task chains 116 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data set 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, and the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 3, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training data set 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data set 304.

Referring to FIG. 1, computing device 104 may calculate, using the plurality of user metrics 128 generated by a stress machine-learning model 116, stress score 120. A "user metric," as used in this disclosure, is a numerical value such as a metric, score, function, or the like, that mathematically delineates, describes, measures, summarizes, or otherwise captures at least an element of user data 108 of the plurality of user data 108 as it may relate to an affective response, user event, stress level, threshold, or the like, of a user in describing stress and/or stressors by quantifying and assigning numerical values to elements and/or variables identified in the data, extracting these elements and/or variables, and calculating by use of an equation, function, heuristic, or the like, as determined by a machine-learning model, a metric as it relates to stress in a user. For instance in non-limiting illustrative examples, a user metric 128 may relate to user stress levels of various physiological elements of data, for instance a number assigned to a user's 'stress from sleep quality' wherein the stress machine-learning model trained with data that relates the user's current sleep schedule and rapid-eye movement (REM) cycle with the user's sleep quality. In further non-limiting illustrative examples, such a user metric for 'stress from sleep quality' may be a function where the metric is a daily average of REM cycle sleep durations calculated from a week of sleep data subtracted by a daily average REM cycle recommendation duration for the user based on the user data 108 that a stress machine-learning model may have stored and/or retrieved from a user database 122; such a resulting metric may be a summation of that series of numerical values, resulting ultimately in either a negative number representing a deficit in sleep amount for that week, or a positive number representing a sleep surplus for the week. In such an example, a user metric 128 may be related to a signifier, identifier, function, and the like that relates such a metric to an associated value for "stress level", for instance and without limitation, a more severe sleep deficit may provide a much higher stress level impact on an exponential scale, wherein acute sleep deficit (missing 1-2 hours of sleep on one 1-2 occasions per week) may be related to more mild stress levels when compared with chronic sleep deficit (1-2 hours of sleep nearly every day). A user metric 128 for 'sleep quality' and its associated relationship to the metric of 'stress level' as determined may represent separate user metrics 128, or be contained within a single user metric 128 for 'stress level from sleep quality.

Continuing in reference to FIG. 1, calculating a stress score 120 may include using a mathematical expression to summarize the plurality of user metrics and may further include at least a user event corresponding to at least a user stress score 120. A plurality of user metrics 128, as described above, may be added, combined, or otherwise included together to generate a stress score 120. A "stress score," as used in this disclosure, is a numerical value aggregate of a plurality of user metrics 128 as it relates to a score of the user's overall stress level, in which the aggregate describes the severity, magnitude, and the identity of the stressors contributing to the user's total stress level; the total stress level may be used for directly comparing a threshold to determine a stress imbalance, as described in further detail below. A stress machine-learning model 116 may calculate a stress score 120 from a plurality of user metrics 128, for instance and without limitation, by normalizing or weighting user metric scores based on impact or contribution to the stress score 120 according to relationships determined from the training data, adding the user metric scores 128 together, using a generated function that relates a first user metric 128 to a second user metric 128 to combine the metrics into a single score, among other ways of arriving at a single stress score 120. In non-limiting illustrative examples, a stress score 120 may be an aggregate determined by a computed average of a plurality of user metrics 128.

Figure 4:
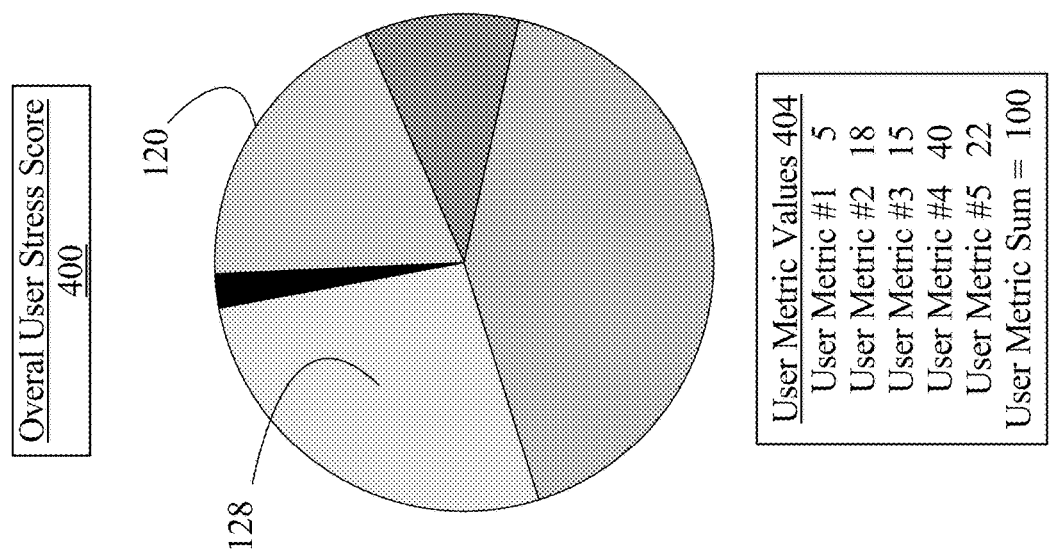
FIG. 4 is a diagrammatic representation of an exemplary embodiment of a graphical display of a user stress score and user metrics.

Referring now to FIG. 4, a non-limiting exemplary embodiment of an overall user stress score 400 is illustrated. An overall user stress score 400 may be a graphical representation of a user stress score 120 that is a combination of a variety of user metric values 404. In the non-limiting example illustrated in FIG. 4, there is a user score 120 that represents the summation of five user metrics 128 that relate to an overall user stress score 400, which may be represented as sections of a pie graph, wherein the user score 120 equals 100. In such an example, each user metric 128 of the five illustrated metrics (shaded areas of the pie chart) may be normalized, weighted, or otherwise treated by the stress machine-learning model 116 to arrive at a user score 120 that may be presented in a pie chart with a total value of 100.

Referring now to FIG. 1, computing device 104 may determine a stress imbalance 132 using the stress score 120, wherein determining the stress imbalance 132 may include calculating differences between at least a user metric 128 and at least a normal stress range determined by the imbalance machine-learning model 136. A "stress imbalance," as used in this disclosure, is a qualitative and/or quantitative determination made between a user stress score 120 and a normal stress range, wherein an imbalance signifies increased levels of user stress over a normal range. A "normal stress range," as used in this disclosure, is a range of stress metrics, or threshold value of stress score, that may be considered a normal, healthy, or otherwise beneficial target range for a user given their user data 108. Such a normal stress range may be the same across users and/or may vary between users depending upon associated user data 108. An imbalance machine-learning model 136 may calculate a normal stress range threshold by considering a user stress score 120 and all associated user data 108, for instance work schedule, demographics, sleep schedule, nutrition deficiencies, age, and the like, to calculate a numerical value that considers a range of stress score values that may be attainable for a user, with a threshold cutoff outside which the user may be considered to possess a stress imbalance 132. For instance and without limitation, an imbalance machine-learning model 136 may calculate a normal stress range threshold by training with data retrieved from a database that relates user data 108 to 'normal stress range' numerical values similar to how user data 108 corresponds to user metrics 128, which may be represented by a range of values; the trained imbalance machine-learning model 136 may then determine a numerical threshold associated with the range, for instance the upper or lower value of the numerical range, above and/or below which may be considered a stress imbalance 132, wherein the user is experiencing an amount of stress which may have deleterious effects on user physiology, emotion, lifestyle, and the like. In further non-limiting illustrative examples, an imbalance machine-learning model 136 may accept an input of a user stress score 120 and train using data relating current user stress scores 120, for instance from one or more users, and determine a stress range as it relates to the scoring criteria, and ultimately calculate a stress score 120 threshold for determining if a stress imbalance exists. An imbalance machine-learning model 136 may calculate a difference between a threshold and one or more individual user metrics 128 used to compute the user stress score 120, to determine a stress imbalance 132. For instance and without limitation, an imbalance machine-learning model 136 may determine a numerical stress threshold associated with a normal stress range for quantifying a stress imbalance associated with sleep deprivation; a user metric 128 with user data 108 regarding sleep quality may be used corresponding with the normal stress range values for sleep deprivation, and an imbalance machine-learning model 136 may determine a threshold value from this data, wherein comparing the user metric 128 to the threshold may reveal a stress imbalance 132.

The imbalance machine-learning model 136 may determine, using the calculated difference between the user metric 128 and the range of normal stress, at least an imbalance, wherein determining at least an imbalance further comprises determining the severity of the imbalance as a function of the calculated difference. An imbalance machine-learning model 136 may determine a threshold value from a numerical range of stress that may be considered normal, adequate to health, or otherwise beneficial to a user, as described above. Such an imbalance machine-learning model 136 may then determine the severity of an imbalance as the imbalance corresponds to the threshold. For instance and without limitation, an imbalance machine-learning model 136 may determine a range of numerical values which corresponds to user stress scores 120 and/or user metrics 128 that are considered normal, and train with data relating user stress scores 120 of populations similar to a user to calculate standard deviations, confidence intervals, and/or other statistical models for comparing a single user stress scores 120 to a population of scores to determine the severity of a stress imbalance. For instance, severity of an imbalance may scale with the probability of a stress score 120 representing an outlier, or significant deviation from an average score, a normal distribution of scores, and the like.

The imbalance machine-learning model 136 may identify at least a user experience that contributes to a stress imbalance 132, wherein identifying further comprises determining an impact of at least an event on the user stress score 120. User data 108 may be used as training data to train a stress machine-learning model 116 for determining user metrics 128 as it relates to an overall user stress score 120, as described above. Elements of user data 108 such as user events, experiences, and the like, may correspond to user metrics 128 and/or user stress score 120, as described above, and an imbalance machine-learning model 136 may determine at least an event, experience, and the like, as it relates to an imbalance of a user metric 128 and/or user stress score 120 as it relates to a threshold. In non-limiting illustrative examples, an imbalance machine-learning model 136 may identify at least a user experience that contributes to a stress imbalance, wherein contribute may be a numerical value of impact that relates a user experience to an imbalance. For instance and without limitation, a stress imbalance determined by an imbalance machine-learning model 136 may be calculated by comparing a user stress score 120 to a normal range, wherein the threshold is the upper limit of the range, resulting in a stress imbalance; the stress score 120 may correspond to a particular user experience, such as a work deadline, that if removed from the user data 108 would result in a stress score 120 that falls below the threshold and within the normal range. An imbalance machine-learning model 136 may identify such an event as contributing to the stress imbalance 132. Alternatively or additionally, an imbalance stress machine-learning model 136 may model the effect a user event described in the user data 108 has on a stress imbalance 132 by, for instance and without limitation, determining the effect on a stress imbalance 132 by removing each event individually and/or in combination. In such an example, an imbalance machine-learning model 132 may also determine the impact and/or severity a user event described in the user data 108 has on a user's stress score 120 and or user metrics 128.

Continuing in reference to FIG. 1, determining a stress imbalance 132 may include calculating a chronic stress baseline, wherein the chronic stress baseline 140 corresponds to a basal stress level of a user that contributes to the user stress score. A "chronic stress baseline," as used in this disclosure, is a minimal, basal level of stress that exists due to a combination of user lifestyle, physiology, demographics, and the like, and is not be attributable to particular events in user data 108. In non-limiting illustrative examples, chronic stress baseline 140 may be due to patterns in user lifestyle, for instance due to nutritional deficiencies, long-term sleep quality patterns, nature of profession, and the like, which may be quantified but not attributed to a single event; chronic stress baseline may be determined from recurring lifestyle events such as a daily commute that reduces leisure activity. An imbalance machine-learning model 136 may determine a normal stress range and/or a stress threshold by determining a chronic stress baseline 140 and determining the minimal, acceptable basal stress level a user score 120 may have according to user data 108.

Continuing in reference to FIG. 1, determining a stress imbalance 132 may include determining an acute stress level 144, wherein an acute stress level 144 is attributed to at least a user event that contributes to the user stress score 120. An "acute stress level," as used in this disclosure, is a level of stress that exists due to a user experience, event, and the like, and may be attributable to particular events in user data 108, wherein the presence of the symptoms develop quickly but do not last long enough to establish a new chronic baseline of stress. In non-limiting illustrative examples, acute stress level 144 may be due to isolated events, single events such as the death of a loved one, and/or patterns of events such as increased anxiety and stress each month when rent is due. In further non-limiting illustrative examples, an acute stress level 144 associated with rent payment may be attributed to user data 108 for instance from heart rate, sleep quality, and other physiological parameters detected from a wearable device, as it relates to the date each month when a user must pay rent; likewise a single life event such as the death of a loved one, or a professional review may be attributed by a stress machine-learning model 116, as described above, to a calculated numerical value of stress, such as a user metric 128 and/or how it relates to a user's stress score 120. Such an event may then have a numerical impact associated with it, which an imbalance machine-learning model 136, as described above, may compare with a user stress 'normal range' and/or threshold to determine if the impact and/or severity of the stress on a user imbalance; where "severity" is a quantitative measure indicating magnitude of symptoms associated with stress. In non-limiting illustrative examples, a user chronic stress baseline 140 may place a user within a normal stress level and within a threshold for determining a stress imbalance, but an acute stress level 144 may place a user above such a threshold during periods with the acute stress increases; this may result in a stress imbalance that is periodic and attributed, in part, to the acute stress level 144. In such an example, potential stress management strategies may be to ablate and/or remove the acute stressor and/or reduce the chronic stress baseline 140 so that the chronic stress baseline 140 in addition to the acute stress level 144 is within the threshold, among other strategies, as discussed in more detail below.

Figure 5:
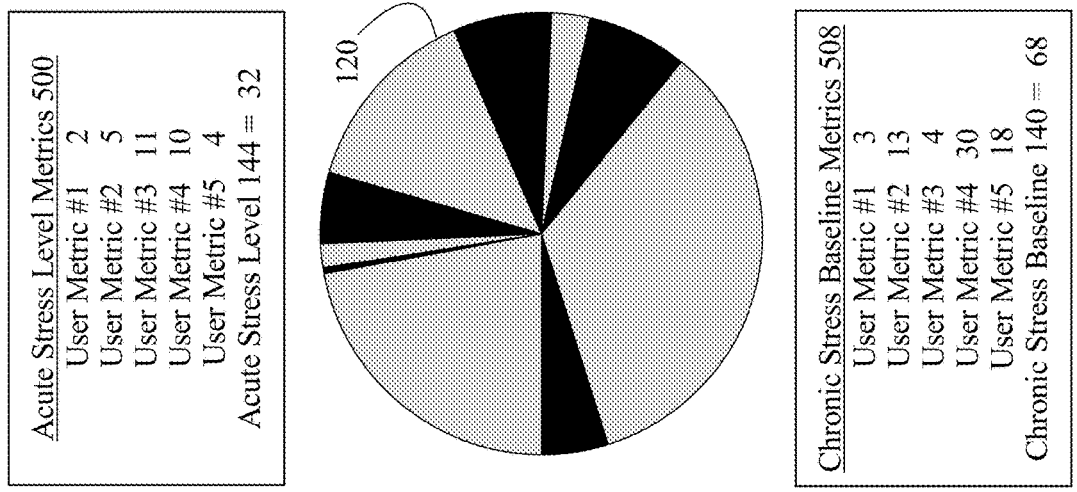
FIG. 5 is a diagrammatic representation of an exemplary embodiment of a graphical display of acute stress level and chronic stress baseline of a user.

Referring now to FIG. 5, an exemplary embodiment of acute stress level metrics 500 and chronic stress baseline metrics 508 is illustrated. Each user metric 128 of a user stress score 120 may have a value associated with it that may be attributed to an acute stress level 144 (denoted as black shaded regions in the pic chart). Acute stress level metrics 500 may be calculated for each user metric 128 (five user metrics 128 are illustrated); each user metric 128 may not have an acute stress level 144 value associated with it, and likewise, each user metric 128 may have more than one user experience and/or event that corresponds to the acute stress level. Chronic stress baseline metrics 504 may be calculated for each user metric 128. Each user metric 128 may have a value associated with it that may be attributed to a chronic stress baseline 140 (denoted as the light grey shaded regions). The summation of the chronic stress baseline metrics 128 from a plurality of user metrics 128 may result in a numerical value that corresponds to the user chronic stress baseline 140. In the example illustrated in FIG. 5, five user metrics 128 corresponds to a user stress score 120 of a value of 100, with 68% of the user stress attributed to chronic stress, which pertains to the baseline level of stress the user maintains, and 32% of the user stress score 120 is attributed to acute stress linked to particular events in the user's life.

Referring now to FIG. 1, computing device 104 may generate a stress balance instruction set 148, wherein generating the stress balance instruction set 148 may include training an instruction machine-learning model 152 as a function of instruction training data 124, wherein training data 124 correlates stress imbalance data to strategies for addressing stress imbalance 132. A stress balance instruction set 148 may be trained, as described above, with instruction training data 124, wherein the training data 120 may be retrieved from a user database 112, online source, research repository, and the like. In non-limiting illustrating, a machine learning module 300 may include a query for stress management strategies relating to a user stress score and any events contributing to the score, and train an instruction machine-learning model 152 as a function the strategies that were returned and the user data 108 that contributed to the score. An instruction machine-learning model 152 may generate a stress balance instruction set 148 as a function of the training. Such a stress balance instruction set 148 may represent a set of instructions, increments, steps, and the like, that a user may follow to implement a stress management strategy that is identified by an instruction machine-learning model 152.

Continuing in reference to FIG. 1, generating a stress balance instruction set 148 may include retrieving training data 124 corresponding to a plurality of stress management strategies in addressing at least a stress imbalance 132 from a database using a classifier generated by a classification algorithm 156. Training data 124 may be filtered, sorted, and/or selected using one or more supervised and/or unsupervised machine-learning processes and/or models as described in above; such models may include without limitation a training data classifier 316. Training data classifier 316 may include a "classifier," which as used in this disclosure is a machine-learning model as defined above, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm 156, defined as a process whereby a computing device and/or any module and/or component operating thereon derives a classifier from training data set 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data 124 to match one or more categories including elements of user data and/or constitutional data, such as without limitation a cohort of persons and/or other analyzed items and/or phenomena for which a subset of training data may be selected.

Continuing in reference to FIG. 1, computing device 104 may train the instruction machine-learning model 152 as a function of the training data classifier 316. The instruction machine-learning model 152 may be trained as a function of the training data classifier 316, as described above, wherein the training data classifier 316 may correspond to a set of stress management strategies relating to various levels of efficacy in addressing a stress imbalance 132, altering a stress score 120, addressing an event related to a stress score 120 and/or stress metric 128, and the like. A training data classifier 316 may include data corresponding to user outcomes associated with a stress management strategy, such as anticipated impact on a stress imbalance, user stress score 120, user metric 128, and the like. A training data classifier 316 may be stored and/or retrieved from a user database 112 for training subsequent machine-learning models.

Continuing in reference to FIG. 1, computing device 104 may identify, as a function of the stress imbalance 132 and the instruction machine-learning model 160, at least a strategy for addressing a user stress imbalance 132, wherein the instruction machine-learning model 160 may identify a plurality of instructions to implementing a stress management strategy to address a stress imbalance. The instruction machine-learning model 160 trained with the training data classifier 316 may accept an input of a stress imbalance 132 and identify at least a stress management strategy for addressing the stress imbalance 132. Identifying a stress management strategy may include selecting stress management strategies based on anticipated impact on stress score 120, user event, and/or user metric 128, ease of adopting the strategy according to instruction set, user input, and the like.

Continuing in reference to FIG. 1, computing device 104 may generate an instruction set for a user to implement a strategy for addressing the stress imbalance 132, as a function of the at least a strategy. The instruction machine-learning model 160 may identify a stress management strategy for addressing a stress imbalance 132, wherein the strategy can be communicated to a user as a series of instructions. A "stress balance instruction set," as used herein, is a series of instructions for implementing at least a stress management strategy according to the user data 108 that is available to the computing device 104, wherein the 'stress management strategy' is at least a strategy for addressing a user stress imbalance 132. Instructions may describe steps to implementing a stress management strategy, for instance and without limitation, a user stress imbalance may be due to a high-impact, high-severity acute stress event of losing a loved one, and the stress management strategy instructions may be to 'gather photographs to make a scrapbook', 'collect the belongings you wish to keep', and 'give away their other belongings to those who can make use of them', wherein completing each instruction may have an effect on the user stress score 120, stress imbalance 132, and/or the acute stress level. User data 180 may be used to determine the instructions for an instruction set for implementing a stress management strategy. Alternatively or additionally, an instruction machine-learning model 160 may retrieve the instructions to implementing the strategy from a user database 112, online repository, or the like, such as was done for the training data classifier for the machine-learning model.

Continuing in reference to FIG. 1, computing device 104 may generate a stress balance instruction set 148 by using a ranking function to prioritize instructions corresponding to impact on at least an imbalance as a function of the ranking of severity of the plurality of imbalances. As described herein, an instruction machine-learning model 160 may use a ranking function, where a ranking function may be a type of objective function that provides a rank, wherein the rank is a quantitative value assigned to an instruction based on a severity of stress, impact on stress imbalance 132, chronological steps in completing a task, difficulty to implementing the instruction, or the like. A ranking of a set of instructions for a plurality of stress management strategies may be, for instance and without limitation, a set of quantitative numerical values arranged in order of increasing value. Set of instructions may alternatively or additionally be arranged in a manner that describes a chronology of implementation of steps to be undertaken to get an intended effect. A "ranking function," as described herein may refer to an objective function, wherein an objective function may include performing a greedy algorithm process. A "greedy algorithm" is defined as an algorithm that selects locally optimal choices, which may or may not generate a globally optimal solution, and then such a ranking function would then rank the instructions of the stress balance instruction set 148 based upon the optimal listing. For instance, computing device 104 may select instructions so that scores associated therewith are the best score for ranking each instruction, wherein the score relates to a numerical impact, and the ranking is based on increasing impact score. For instance and without limitation, an instruction machine-learning model 160 may rank each identified stress management strategy for each stress imbalance 132 as a function of impact of the strategy on mitigating the imbalance and the severity of the imbalance, and rank each instruction associated with each strategy according. In such an example, instructions may be prioritized into an instruction set corresponding to impact on at least an imbalance and/or as a function of the ranking of severity of the plurality of imbalances.

Alternatively or additionally, in non-limiting illustrative examples a ranking function may be a linear objective function, wherein the computing device 104 may solve using a linear program, such as without limitation, a mixed-integer program. A "linear program," as used in this disclosure, is a program that optimizes a linear objective function, given at least a quantifier and/or ranking score based on impact of an instruction on a user metric 128, user stress score 120, and/or stress imbalance 132; a linear program may be referred to without limitation as a "linear optimization" process and/or algorithm. For instance, in non-limiting illustrative examples, a linear program may use a linear objective function to calculate impact for a level of performing stress management strategy and rank the instructions of each strategy accordingly. A mathematical solver may be implemented to solve for the set of instructions that maximizes impact scores; mathematical solver may be implemented on computing device 104 and/or another device in system 100, and/or may be implemented on third-party solver. A ranking function may include minimizing a loss function, where a "loss function" is an expression of an output of which a ranking process minimizes to generate an optimal result. As a non-limiting example, computing device 104 may assign variables relating to a set of parameters, which may correspond to instruction impact score components and stress score components, as described above, calculate an output of mathematical expression using the variables, and select an objective, or set of instructions, that produces an output having the lowest size, according to a given definition of "size," of the set of outputs representing each of plurality of candidate ingredient combinations; size may, for instance, included absolute value, numerical size, or the like. For instance in non-limiting examples, a loss function may rank an optimal set of instructions based upon how each instruction in a plurality of stress management strategies may reduce the user stress score 120 to a minimal numerical value. Selection of different loss functions may result in identification of different potential pairings as generating minimal outputs. Persons skilled in the art, upon reviewing the entirety of this disclosure, will be aware of various embodiments in which a ranking function may take form and be used by an activity machine-learning model 136 to rank activities of a program 140 based on some criteria as it relates to a user score.

Continuing in reference to FIG. 1, computing device 104 may provide to a user a prioritized stress imbalance 132 and a stress balance instruction set 148 for addressing a stress imbalance 132.

Figure 6:
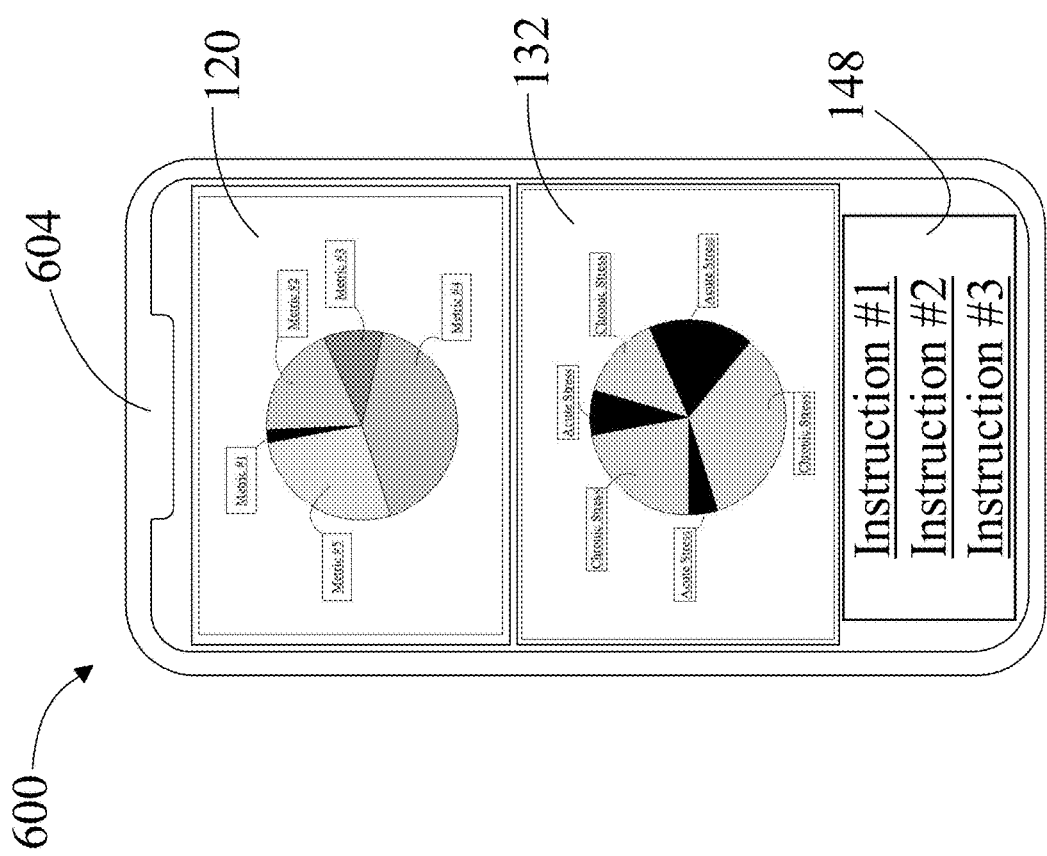
FIG. 6 is a diagrammatic representation an exemplary embodiment of a user device.

Referring now to FIG. 6, an exemplary embodiment 600 of a computing device 104 providing, via a user device 604, the prioritized stress imbalance 132 and the stress balance instruction set 148 for addressing a stress imbalance 132 is illustrated. User device 604 may communicate with computing device 104 via a user database 112, server, or the like, as described in further detail below. User device 604 may display user metrics 128, stress scores 120, stress imbalances 132, stress balance instruction sets 148, and/or any associated data via a graphical user interface (GUI) and/or any other suitable means for displaying graphics, tables, text, or the like. User device 604 may prompt a user to input user data 108, or may prompt a user to transfer, upload, or otherwise communicate recorded wearable device data. Persons skilled in the art, upon reviewing the entirety of this disclosure, will be aware of various ways in which information may be displayed by a user device 604 and/or may prompt a user to enter data, and the various ways in which data may be entered via a user device 604.

Referring not to FIG. 1, computing device 104 may determine the effectiveness of at least an instruction of a stress balance instruction set 148 by receiving, from the user, updated user data 160, wherein updated user data 160 is more recent in time than a provided stress balance instruction set 148. Updated user data 160 may refer to data that is like user data 180 that was used to determine the user metrics 128, user stress score 120, stress imbalance 132, and/or instruction set; updated user data 160 may correspond to wearable device data, user feedback that corresponds to implementing an instruction, or the like. Update user data 164 may be received by a user device 604, as described above. The "effectiveness" of an instruction, as used in this disclosure, is a qualitative and/or quantitative measure of efficacy of an instruction, set of instructions, and/or strategy that corresponds to a set of instructions in addressing a stress imbalance, altering a user stress score 120, and/or impacting a user metric 128; effectiveness may be represented as a numerical value, function, matrix, vector, signifier, or any other suitable means by which a machine-learning process, computing device, or the like may refer to an effectiveness metric of an instruction. In non-limiting illustrative examples, effectiveness of an instruction may refer to recognizing user feedback in the updated user data 160 that relates to a user's reported effectiveness of a stress management strategy and/or instruction; for instance, a user may directly report that they did not like a strategy, prefer a second strategy, or found an instruction effective.

Continuing in reference to FIG. 1, computing device 104 may recalculate, using an effectiveness machine-learning process 164, a first stress score 120 and the updated user data 160, an updated stress score 168 as a function of the updated user data 160. The effectiveness metric corresponding to an instruction and/or strategy may be determined by an effectiveness machine-learning process 164, wherein the effectiveness machine-learning process 164 accepts an input of a first user stress score 120 and the updated user data 160 and recalculates how a plurality of user metrics 128 may have been impacted as reflected by the updated user data 160. For instance in non-limiting illustrative examples, the effectiveness machine-learning process 164 may retrieve from a user database 112 a stress machine-learning model to train the model with the updated user data 160 to determine any change between a first set of user metrics 128 and a second set of user metrics 128 from the updated user data 160. In such an example, the resulting user metrics 128 from the updated user data 160 may corresponds to a second user stress score 120, which may be compared to a first user stress score 120. Alternatively or additionally, an effectiveness machine-learning process 164 may take a first user stress score 120 and additively or subtractively increase a score according to a previous machine-learning model as a function of each new element of updated user data 160 as it corresponds to a first set of user data 108. For instance in non-limiting illustrative examples, a first set of user data 108 may contain physiological wearable device data that corresponds to blood pressure and heart rate throughout the work week, and a user may have adopted a meditation and mindfulness technique throughout the work week, and the updated user data 160 may contain similar wearable device data that shows decreased blood pressure and heart rate; such updated user data 160 may directly correspond to the user stress score 120 via a relationship determined by a previous model, as described above, and may be retrieved from a user database 112 and used by an effectiveness machine-learning process 164 directly to recalculate the user stress score 120.

Continuing in reference to FIG. 1, computing device 104 may identify a difference between a first stress score 120 and an updated stress score 168 as a function of an element of the updated user data 160. An effectiveness machine-learning process 164 may recalculate an updated stress score 168 using a first stress score 120 and updated user data 160 as inputs, wherein at least an element of the updated user data 160 may be recorded for some change in score. A change in score may be no change in numerical value from a first user stress score 120 to an updated stress score 168. In non-limiting illustrative examples, a change of an element of user data 108 reflected in the updated user data 160 that results in no change in user stress score may be identified by an effectiveness machine-learning process 164 as a low-impact instruction, activity, physiological metric, or the like; likewise, a change of an element of user data 108 reflected in the updated user data 160 that results in a change in user score may be identified as an instruction, or a non-instruction element of user data relating to an instruction, that has some impact on user score and effectiveness.

Continuing in reference to FIG. 1, computing device 104 may determine how the element of updated user data 160 corresponds to an instruction of the stress balance instruction set 148. The effectiveness machine-learning process 164 may determine a qualitative effect of an element of updated user data 160 corresponds to an instruction of the stress balance instruction set 148 such as a 'yes' or 'no' confirmation that an element of updated user data 160 had an impact corresponding to an instruction of a plurality of instructions, and/or a quantitative metric that corresponds to an instruction such as a numerical value that relates what level an element of user data corresponds to an instruction that was identified to have an effect on a user score. In non-limiting illustrative examples, the effectiveness machine-learning process may determine from the updated user data 160 corresponding to an instruction, which of the plurality of instructions may have been performed, avoided, attempted but not completed, or the like, by the user.

Continuing in reference to FIG. 1, computing device 104 may determine the effectiveness of at least an instruction of a stress balance instruction set 148 by determining the impact of at least a user action datum in contributing to the stress imbalance 132. A "user action datum," as used herein refers to any element of updated user data 160 that describes an action, activity, effort, or the like, that a user has performed, or is performing, in affecting the stress imbalance 132, stress score 120, and/or individual user metrics 128. A user action datum may correspond to an action of implementing an instruction or may correspond to a user action that is not directed to an instruction. An effectiveness machine-learning process 164 may accept an input of a plurality of updated user data 160, for instance retrieved from a user database 112, and determine if a user action is present in the data, such as implementing an instruction, or wearable device data that corresponds to sleep patterns, exercise, or the like. The effectiveness machine-learning process 164 may determine the effect of each user action qualitatively, such as a 'yes, user action has an effect' or 'no effect', and/or quantitatively, such as a numerical value of impact on a stress score 120, user metric 128, and the like. The effectiveness machine-learning process 164 may perform a recalculation of the updated stress score 168 using user actions to determine the effect that the user behavior and/or instruction implementation has had on the original stress score 120. A user may have performed a user action reflected in the updated user data 160 that corresponds to a change in the stress score 120 that was not suggested by the stress balance instruction set 148; likewise the user action may correspond directly to an instruction, as described above. In non-limiting illustrative examples, a stress balance instruction set 148 may suggest a series of user actions for improving sleep quality, such as 'no electronic device use within 2 hours of sleep', 'taking a warm bath 1.5 hour before sleep', 'meditating for 15 minutes 1 hour before sleep', and 'taking 10 mg of melatonin 45 minutes before sleep', wherein completing these actions may be reflected indirectly via a wearable sleep monitoring device that shows an increase in the sleep quality over time, and that this may be attributed to a user indicating that the instructions were performed. In such an example, the newly adopted bedtime routine suggested via an instruction set may result in wearable device data that shows the user's sleep quality has improved; such user actions may then have a quantitative impact on stress score 120, reflected in the updated stress score 168.

Continuing in reference to FIG. 1, computing device may calculate the likelihood to implement an instruction for a user by considering how past user events corresponds to following an instruction of a stress balance instruction set 148. The "likelihood" to implement an instruction, as described in this disclosure, is a probabilistic quantitative metric that reflects a tendency for a user to follow an instruction, course of action, stress management strategy, or the like. An effectiveness machine-learning process 164 may determine how user actions reflected in the updated user data 160 correspond to implementing the instructions in a stress balance instruction set 148, and calculate the likelihood of implementing an instruction, wherein the likelihood changes over time with more user data. In non-limiting exemplary embodiments, the effectiveness machine-learning process 164 may accept an input of updated user data 160 and retrieve a first element of user data 108 for instance from a user database 112, and track user actions in addressing stress over time, wherein the effectiveness machine-learning process 164 may determine which actions a user is more likely to perform in addressing a stress imbalance 132, and the effectiveness machine-learning process 164 may calculate the a corresponding likelihood. The effectiveness machine-learning process 164 may then use information relating the likelihood of a user to adopt a strategy or perform an instruction to update, modify, or otherwise calculate the effectiveness and/or the predicted effectiveness of an instruction and/or stress management strategy. For instance in non-limiting illustrative examples, a stress balance instruction set 148 may suggest a series of actions regarding the use of meditation to alleviate stress in a user, wherein past user events may suggest that the user has an aversion to meditative techniques and is not likely to force a habit of meditation. In such an example, an effectiveness machine-learning process 164 may determine that whenever meditation is found in an instruction set, the user is not likely to implement those instructions, and may adjust the determined effectiveness metric accordingly. This may be performed, as described above, by receiving updated user data 160 and determining how it relates to implementing an instruction by using an effectiveness machine-learning process 164. User likelihoods calculated by an effectiveness machine-learning process 164 may be stored and/or retrieved from a user database 112 to inform other steps of the system 100, for instance and without limitation, to train an instruction machine-learning model 152.

Continuing in reference to FIG. 1, computing device 104 may use the determined effectiveness of at least an instruction set output by the effectiveness machine-learning process 164 to update a stress balance instruction set 148 as a function of the calculated effectiveness of a strategy for addressing a stress imbalance 132. A stress balance instruction set 148 may be iteratively updated to reflect changes in the updated user data 160, updated stress score 168, and the calculated effectiveness and likelihood of user actions in implementing an instruction of a stress balance instruction set 148. In non-limiting illustrative examples, effectiveness and/or likelihood metrics of user actions reflected in the updated user data 160 may be used to train an instruction machine-learning model 152 to retrieve new instructions, eliminate instructions, and/or otherwise modify instructions based upon the effectiveness of and/or likelihood to implement past instructions. In further non-limiting illustrative examples, user chronic stress and acute stress metrics may be iteratively updated based upon implementing an instruction and its associated effectiveness and/or likelihood metrics; for instance there may be an increase in acute stress from a user experiencing a burden in adopting an instruction, wherein the instruction may have a net positive effect on stress imbalance 132, but implementing the instruction is a financial burden, decreases leisure activity for a user, represents a time commitment, and the like. In such an example, this instruction may be updated with a second instruction that may represent a more effective strategy.

Figure 7:
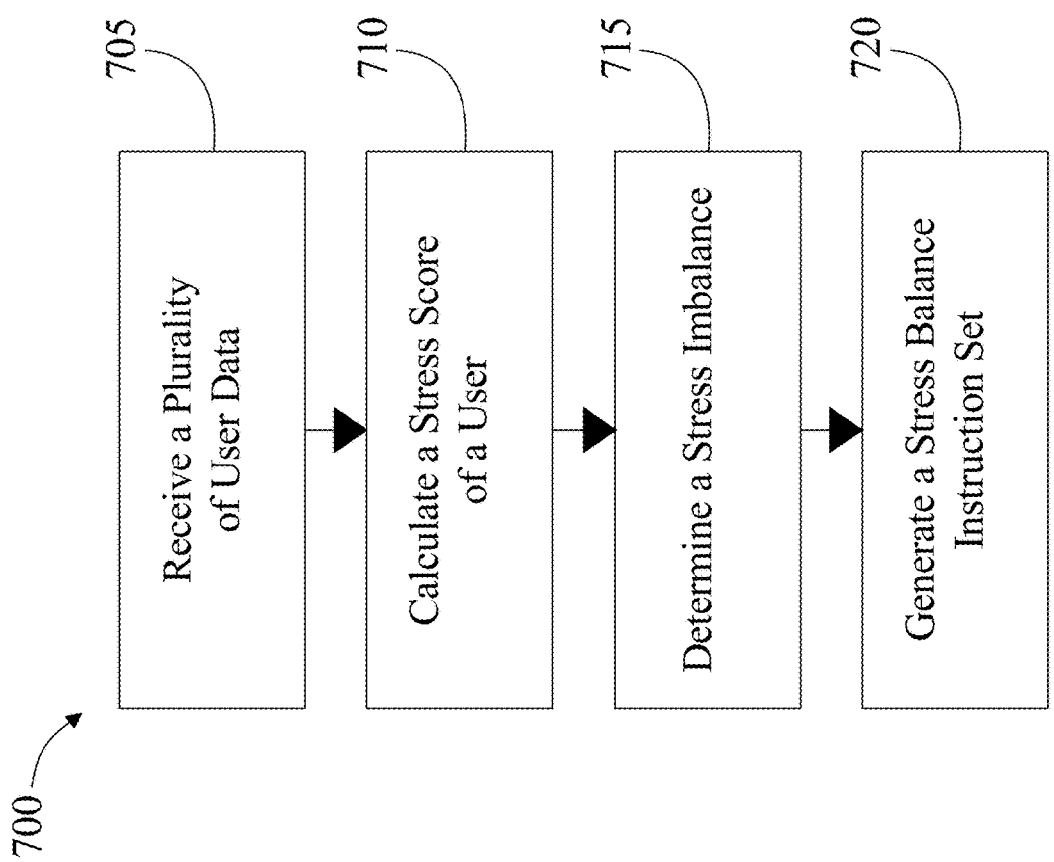
FIG. 7 is a flow diagram illustrating an exemplary workflow of a method for generating a stress balance instruction set for a user.

Referring now to FIG. 7, an exemplary embodiment of a method 700 for generating a stress balance instruction set for a user is illustrated. At step 705, computing device 104 may receive a plurality of user data 108. User data 108 may include at least an element of user-reported data from a questionnaire, and/or at least an element of data retrieved from a wearable device, and/or an element of data relating to an affective measure, behavioral cue, physiological data, and the like, as described herein; this may be implemented, without limitation, as described above in reference to FIGS. 1-6.

At step 710, computing device 104 may calculate, using a stress machine-learning model 116 and a plurality of user data 108, a stress score 120 of a user. Calculating a stress score may include training a stress machine-learning model 116 as a function of stress score training data 124, wherein training data 124 includes a plurality of entries, and each entry correlates user data to at least a user metric that numerically describes stress in a user, generating a plurality of user metrics as a function of the plurality of user data and the stress machine-learning model, and calculating, using the plurality of user metrics, an stress score 120; this may be implemented, without limitation, as described above in reference to FIGS. 1-6.

At step 715, computing device 104 may determine a stress imbalance 132 using the overall user stress score 120. Determining a stress imbalance further comprises calculating a chronic stress baseline, wherein the chronic stress baseline corresponds to a basal stress level of a user that contributes to the user stress score. Determining a stress imbalance further comprises determining an acute stress level, wherein an acute stress level is attributed to at least a user event that contributes to the user stress score; this may be implemented, without limitation, as described above in reference to FIGS. 1-6.

At step 720, computing device 104 may generate a stress balance instruction set 148, wherein generating the stress balance instruction 148 set may include training an instruction machine-learning model 152 as a function of instruction training data 124, wherein training data 124 correlates stress imbalance 132 data to strategies for addressing stress imbalance, identifying, as a function of the stress imbalance 132 and the instruction machine-learning model 152, at least a strategy for addressing a user stress imbalance 132, and generating an instruction set for a user to implement a strategy for addressing the stress imbalance 132, as a function of the at least a strategy. Generating a stress balance instruction set 148 using the instruction machine-learning model 152 may include retrieving training data 124 corresponding to a plurality of stress management strategies in addressing at least a stress imbalance 132 from a user database 112 using a classifier generated by a classification algorithm 156, training the instruction machine-learning model 152 as a function of the training data classifier 316, and identifying a plurality of instructions to implementing a stress management strategy to address a stress imbalance 132. Generating a stress balance instruction set 148 using the instruction machine-learning model 152 may include retrieving training data 124 corresponding to a plurality of stress management strategies in addressing at least a stress imbalance 132 from a user database 112 using a classifier generated by a classification algorithm 156, training the instruction machine-learning model 152 as a function of the training data classifier 316, and identifying a plurality of instructions to implementing a stress management strategy to address a stress imbalance. Determining the effectiveness of at least an instruction of a stress balance instruction set may include receiving, from the user, updated user data 160, wherein updated user data 160 is more recent in time than a provided stress balance instruction set 148, recalculating, using an effectiveness machine-learning process 164, a first stress score 120 and the updated user data 160, an updated stress score 168 as a function of the updated user data 160, identifying a difference between a first stress score 120 and an updated stress score 168 as a function of an element of the updated user data 160, and determining how the element of updated user data 160 corresponds to an instruction of the stress balance instruction set. Determining the effectiveness of at least an instruction of a stress balance instruction set 148 may include receiving, from the user, updated user data 164, wherein updated user data 160 is more recent in time than a provided stress balance instruction set 148, recalculating, using an effectiveness machine-learning process 164, a first stress score 120 and the updated user data 160, an updated stress score 168 as a function of the updated user data 160, identifying a difference between a first stress score 120 and an updated stress score 168 as a function of an element of the updated user data 160, and determining how the element of updated user data 160 corresponds to an instruction of the stress balance instruction set 148. Determining effectiveness of at least an instruction set output by the effectiveness machine-learning process 164 to may include updating a stress balance instruction set 148 as a function of the calculated effectiveness of a strategy for addressing a stress imbalance; this may be implemented, without limitation, as described above in reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
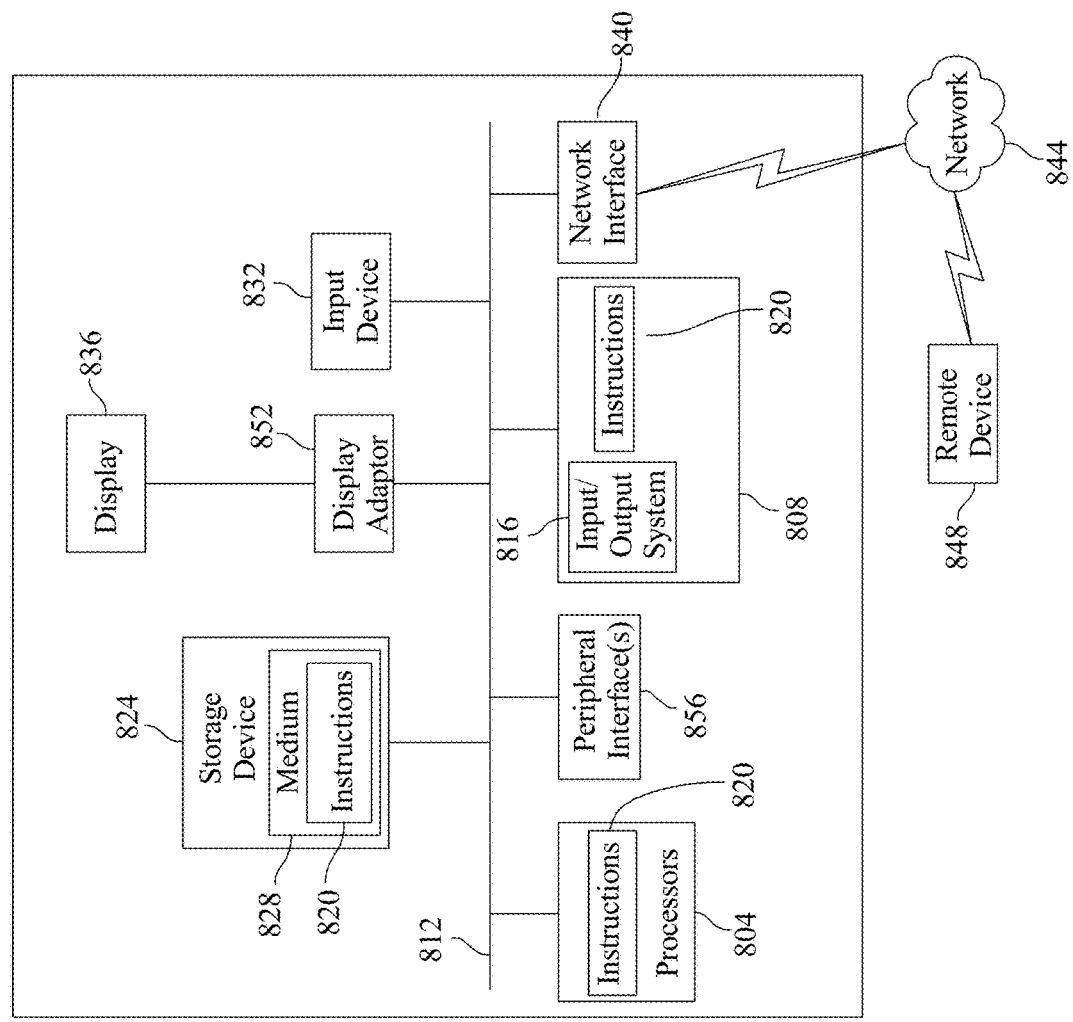
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a stress balance instruction set for a user, the system comprising a computing device, wherein the computing device is configured to:
   receive a plurality of user data;
   calculate, using a stress machine-learning model and the plurality of user data, a stress score of a user, wherein calculating the stress score further comprises:
      training a stress machine-learning model as a function of stress score training data, wherein stress score training data includes a plurality of entries, and each entry correlates user data to at least a user metric that delineates stress in a user;
      generating a plurality of user metrics as a function of the plurality of user data and the stress machine-learning model; and
      calculating, as a function of the plurality of user metrics, a stress score;
   determine a stress imbalance as a function of the stress score;
   generate a stress balance instruction set, wherein generating the stress balance instruction set further comprises:
      training an instruction machine-learning model as a function of instruction training data, wherein instruction training data correlates stress imbalance data to strategies for addressing stress imbalance;
      identifying, as a function of the stress imbalance and the instruction machine-learning model, at least a strategy for addressing a user stress imbalance, wherein identifying the at least a strategy is based on at least an ease of adopting the at least a strategy as a function of the stress balance instruction set; and
      generating the stress balance instruction set as a function of the at least a strategy;
   receive at least a past user action datum, wherein the at least a past user action datum comprises a plurality of user activity data associated with the stress imbalance;
   calculate a likelihood of implementation of an instruction of the stress balance instruction set based on the at least a past user action datum, wherein calculating the likelihood comprises:
      determining user-preferred instructions from the stress balance instruction set; and
      calculating the likelihood of implementation for the user-preferred instructions; and
   determine, using an effectiveness machine learning model, an effectiveness of the instruction as a function of the likelihood of implementation, wherein the effectiveness machine learning model adjusts the effectiveness as a function of the likelihood of implementation.

2. The system of claim 1, wherein calculating the stress score further comprises:
   receiving at least a user event;
   aggregating the plurality of user metrics; and
   calculating the stress score using a mathematical expression evaluating the at least a user event and the aggregated plurality of user metrics.

3. The system of claim 1, wherein determining the stress imbalance further comprises:
   calculating a difference between a user metric, of the plurality of user metrics, and a normal stress range determined by an imbalance machine-learning model;
   determining, using the calculated difference between the user metric and the normal stress range, the stress imbalance, wherein determining the stress imbalance further comprises determining a severity of the stress imbalance as a function of the calculated difference.

4. The system of claim 1, wherein determining a stress imbalance further comprises identifying at least a user experience that contributes to a stress imbalance, wherein the user experience has an impact of at least an event on the user stress score.

5. The system of claim 1, wherein determining the stress imbalance further comprises calculating a chronic stress imbalance.

6. The system of claim 1, wherein determining the stress imbalance further comprises determining an acute stress imbalance.

7. The system of claim 1, wherein generating the stress balance instruction set using the instruction machine-learning model further comprises:
retrieving the instruction training data using a training data classifier.

8. The system of claim 1, wherein generating the stress balance instruction set further comprises:
ranking instructions as a function of severity of a plurality of imbalances; and
providing to a user a prioritized stress balance instruction set as a function of the ranking.

9. The system of claim 1 further comprising:
receiving, from the user, updated user data, wherein updated user data is more recent in time than the stress balance instruction set;
recalculating, using a stress machine-learning process, a first stress score and the updated user data, an updated stress score as a function of the updated user data;
identifying a difference between a first stress score and the updated stress score; and
determining an effectiveness of the stress balance instruction set as a function of the difference between the first stress score and the updated stress score.

10. A method for generating a stress balance instruction set for a user, the method comprising using a computing device, wherein the computing device is configured for:
receiving a plurality of user data;
calculating, using a stress machine-learning model and the plurality of user data, a stress score of a user, wherein calculating a stress score further comprises:
training a stress machine-learning model as a function of stress score training data, wherein training data includes a plurality of entries, and each entry correlates user data to at least a user metric that delineates stress in a user;
generating a plurality of user metrics as a function of the plurality of user data and the stress machine-learning model; and
calculating, using the plurality of user metrics, a stress score;
determining a stress imbalance using the stress score;
generating a stress balance instruction set, wherein generating the stress balance instruction set further comprises:
training an instruction machine-learning model as a function of instruction training data, wherein instruction training data correlates stress imbalance data to strategies for addressing stress imbalance;
identifying, as a function of the stress imbalance and the instruction machine-learning model, at least a strategy for addressing a user stress imbalance, wherein identifying the at least a strategy is based on at least an ease of adopting the at least a strategy as a function of the stress balance instruction set; and
generating the stress balance instruction set as a function of the at least a strategy;
receiving at least a past user action datum, wherein the at least a past user action datum comprises a plurality of user activity data associated with the stress imbalance;
calculating a likelihood of implementation of an instruction of the stress balance instruction set based on the at least a past user action datum, wherein calculating the likelihood comprises:
determining user-preferred instructions from the stress balance instruction set; and
calculating the likelihood of implementation for the user-preferred instructions; and
determining, using an effectiveness machine learning model, an effectiveness of the instruction as a function of the likelihood of implementation, wherein the effectiveness machine learning model adjusts the effectiveness as a function of the likelihood of implementation.

11. The method of claim 10, wherein calculating the stress score further comprises:
summarizing the plurality of user metrics using a mathematical expression; and
including at least a user event corresponding to the stress score.

12. The method of claim 10, wherein determining the stress imbalance further comprises:
calculating a difference between a user metric, of the plurality of user metrics, and a normal stress range determined by an imbalance machine-learning model;
determining, using the calculated difference between the user metric and the normal stress range, the stress imbalance, wherein determining the stress imbalance further comprises determining a severity of the stress imbalance as a function of the calculated difference.

13. The method of claim 10, wherein determining a stress imbalance further comprises identifying at least a user experience that contributes to a stress imbalance, wherein the user experience has an impact of at least an event on the user stress score.

14. The method of claim 10, wherein determining the stress imbalance further comprises calculating a chronic stress imbalance.

15. The method of claim 10, wherein determining the stress imbalance further comprises determining an acute stress imbalance.

16. The method of claim 10, wherein generating the stress balance instruction set using the instruction machine-learning model further comprises:
retrieving the instruction training data using a training data classifier.

17. The method of claim 10, wherein generating the stress balance instruction set further comprises:
ranking instructions as a function of severity of a plurality of imbalances; and
providing to a user a prioritized stress balance instruction set as a function of the ranking.

18. The method of claim 10 further comprising:
receiving, from the user, updated user data, wherein updated user data is more recent in time than the stress balance instruction set;
recalculating, using a stress machine-learning process, a first stress score and the updated user data, an updated stress score as a function of the updated user data;
identifying a difference between a first stress score and the updated stress score; and
determining an effectiveness of the stress balance instruction set as a function of the difference between the first stress score and the updated stress score.

* * * * *